United States Patent [19]

Minai et al.

[11] Patent Number: 5,235,068

[45] Date of Patent: Aug. 10, 1993

[54] PROCESS FOR PRODUCING ACYLAROMATIC COMPOUNDS

[75] Inventors: Masayoshi Minai, Moriyama; Michitada Kondo, Kobe; Yuji Ueda, Izumi; Seiichi Kai, Ikoma; Takayuki Higashii, Kishiwada, all of Japan

[73] Assignee: Sumitomo Chemical Company, Limited, Osaka, Japan

[21] Appl. No.: 915,747

[22] Filed: Jul. 21, 1992

Related U.S. Application Data

[63] Continuation of Ser. No. 339,115, Apr. 17, 1989, abandoned.

[30] Foreign Application Priority Data

Apr. 28, 1988 [JP] Japan ............................ 63-107252

[51] Int. Cl.$^5$ ............... C07C 253/30; C07D 207/333; C07D 307/46; C07D 333/22
[52] U.S. Cl. ............................ 548/540; 549/57; 549/59; 549/60; 549/70; 549/72; 549/73; 549/436; 549/468; 549/483; 549/488; 558/230; 558/405; 560/124; 560/138; 560/141; 560/254; 568/319
[58] Field of Search ..................... 549/70, 72, 73, 59, 549/60, 57, 483; 548/540, 483; 568/319; 558/230, 405

[56] References Cited

U.S. PATENT DOCUMENTS

| | | | |
|---|---|---|---|
| 2,460,825 | 2/1949 | Hartough et al. | 549/483 |
| 2,478,484 | 8/1949 | Hartough et al. | 549/70 |
| 2,492,629 | 12/1949 | Hartough et al. | 549/483 X |
| 2,492,630 | 12/1949 | Hartough et al. | 549/70 |
| 2,515,123 | 7/1950 | Hartough . | |
| 2,963,488 | 12/1960 | Webb . | |
| 3,415,843 | 12/1968 | Pachter et al. | 548/540 X |
| 3,707,478 | 12/1972 | Carson | 260/326.3 |
| 3,721,680 | 3/1973 | Carson | 260/326.5 J |
| 3,752,826 | 8/1973 | Carson | 260/326.3 |
| 3,865,840 | 2/1975 | Carson | 260/326.46 |
| 3,952,012 | 4/1976 | Carson | 260/326.47 |
| 4,070,368 | 1/1978 | Carson | 260/326.47 |
| 4,254,043 | 3/1981 | Kuta . | |

FOREIGN PATENT DOCUMENTS

0268820 10/1987 European Pat. Off. .
547279 1/1971 Switzerland .

OTHER PUBLICATIONS

Fieser, et al., Reagents for Organic Synthesis, vol. 3, (1970), pp. 32-33; Wiley-Interscience, N.Y., London, Sidney.
Gulati, et al.; Organic Synthesis, Collective vol. 2, (1943), pp. 522-523, John Wiley & Sons, Inc., N.Y.
Annale der Chemie BAND 504, pp. 267-286, (1933), Unger.
Abstract and Comments on "Methoden der Organischen Chemie" vol. VII/2a 1973 pp. 311-313.
Houben-Weyl "Methoden der organischen Chemic" vol. VII/2a, (1973) Georg Thieme Verlag, Stuttgart "Ketone, Teil 1" pp. 311-331.
J. Org. Chem., 28, pp. 674-679 (1963), Edwards, et al.

Primary Examiner—Joseph Paul Brust
Attorney, Agent, or Firm—Stevens, Davis, Miller & Mosher

[57] ABSTRACT

Acylaromatic compounds

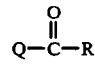

(Q: aromatic compound residue; R: straight, branched or cyclic aliphatic group, aromatic group or araliphatic group) are prepared in high yield by a reaction, in the presence of a boron trifluoride complex catalyst, of an aromatic compound with

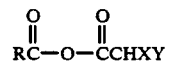

(X: H, Cl, Br; Y: Cl, Br) or with
RCOOH in the presence of (XYCHCO)$_2$O.

26 Claims, No Drawings

PROCESS FOR PRODUCING ACYLAROMATIC COMPOUNDS

This application is a continuation of application Ser. No. 07/339,115, filed Apr. 17, 1989, now abandoned.

The present invention relates to a process for producing acylaromatic compounds represented generally by the following formula

$$Q-\overset{O}{\underset{\|}{C}}-R \quad (I)$$

wherein Q is an aromatic compound residue and R is a straight, branched or cyclic aliphatic group, aromatic or araliphatic group.

The acylaromatic compounds are very important as intermediates of medicines and agricultural chemicals, and are particularly applicable as an intermediate of cholagogue.

The acylaromatic compound can be produced by acylation of an aromatic compound according to Friedel-Crafts Reaction, and the acylation includes the followings;

a) methods of employing an acid chloride and a Lewis acid (aluminum chloride or zinc chloride), b) methods of employing a carboxylic acid anhydride and a Lewis acid, c) methods of employing a carboxylic acid and a polyphosphoric acid, and d) methods of employing a carboxylic acid and trifluoroacetic anhydride (U.S. Pat. No. 4,254,043).

However, the method a) necessitates converting a carboxylic acid into the acid chloride with the use of thionyl chloride etc., and further has problems of disposing waste materials containing aluminum or zinc compounds. For the method b) a carboxylic acid anhydride is to be prepared from the corresponding carboxylic acid, and every carboxylic acid is not necessarily converted to its carboxylic acid anhydride which restrict the acylating agent. Methods c) and d) are meritorious industrially due to their allowance for direct usages of carboxylic acids, however, waste water disposals from the large amount of polyphosphoric acid employed and the usage of extremely expensive trifluoroacetic acid anhydride are problems concerned. As mentioned above, the known industrial method for acylation of aromatic compounds for the production of acylaromatic compounds have not necessarily been satisfactory.

The present inventors have ascertained that acylation of an aromatic compound can be achieved with an industrial advantage by the use or a combination of a mixed acid anhydride or a carboxylic acid with an acid anhydride and a boron trifluoride catalyst.

According to the present invention, there is provided a process for producing an acylaromatic compound of the formula (I), which comprises a reaction, in the presence of boron trifluoride or a boron trifluoride complex catalyst, of an aromatic compound with either a) a mixed acid anhydride represented by the formula (II)

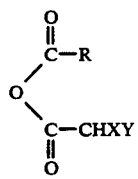

$$\underset{O}{\overset{O}{\underset{\|}{C}-CHXY}}\overset{\overset{O}{\underset{\|}{C}-R}}{\diagdown}\quad (II)$$

wherein R is a straight, branched or cyclic aliphatic group, aromatic group or araliphatic group, in which the straight, branched or cyclic aliphatic group includes an alkyl group having 1 to 18 carbon atoms, an alkenyl group having 2 to 18 carbon atoms, an alkynyl group having 2 to 18 carbon atoms, a cyclic alkyl group having 3 to 8 carbon atoms, a cyclic alkenyl group having 3 to 8 carbon atoms, a cyclic alkynyl group having 3 to 8 carbon atoms, a cycloalkylalkyl group having 3 to 15 carbon atoms, a cycloalkylalkenyl group having 3 to 15carbon atoms, a cycloalkylalkynyl group having 3 to 15 carbon atoms, a cycloalkenylalkyl group having 3 to 15 carbon atoms, a cycloalkynylalkyl group having 3 to 15 carbon atoms and a cycloalkenylalkenyl group having 3 to 15 carbon atoms; the araliphatic group includes a thienylalkyl group, a thienylalkenyl group, an phenylalkyl group, a thienylalkynyl group, a furylalkyl group, a naphthylalkyl group, a furylalkenyl group, an phenylalkenyl group, an phenylalkynyl group, a biphenylylalkyl group, a biphenylylalkenyl group; the aromatic group includes phenyl group, biphenyl group, naphthyl group, thienyl group or furyl group; which araliphatic groups and aromatic groups may optionally be substituted once, twice or three times by alkyl groups having 1 to 12 carbon atoms, alkenyl groups having 2 to 12 carbon atoms, alkynyl groups having 2 to 12 carbon atoms, alkoxyl groups having 1 to 12 carbon atoms, alkenyloxyl groups having 1 to 12 carbon atoms, alkynyloxyl groups having 2 to 12 carbon atoms, methylenedioxy group, ethylenedioxy group, aralkyl groups having 7 to 12 carbon atoms, aralkyloxyl groups having 7 to 12 carbon atoms, phenoxyl group, alkyloxycarbonyl groups having 2 to 9 carbon atoms, alkylcarbonyloxyl groups having 2 to 9 carbon atoms and halogen atoms; which R may have one or more substituents of a hologen atom, an alkyl group having 1 to 10 carbon atoms, an alkenyl group having 2 to 10 carbon atoms, an alkynyl group having 2 to 10 carbon atoms, an alkenyloxyl group having 2 to 10 carbon atoms, an alkynyloxyl group having 2 to 10 carbon atoms, an alkoxyl group having 1 to 10 carbon atoms, an alkanoyloxyl group having 1 to 10 carbon atoms, an aralkanoyloxyl group having 8 to 13 carbon atoms, an alkoxycarbonyl group having 2 to 11 carbon atoms, an aralkoxycarbonyl group having 8 to 13 carbon atoms, an alkanoyl group having 2 to 12 carbon atoms, an aralkanoyl group having 8 to 13 carbon atoms, an alkanoylalkoxyl group having 3 to 13 carbon atoms, alkoxyalkoxyl group having 2 to 12 carbon atoms, methylendioxy group, ethylenedioxy group, an alkylthio group having 1 to 10 carbon atoms, an alkanoylthio group having 2 to 10 carbon atoms, an alkanoylamino group having 2 to 10 carbon atoms, an alkylaminocarbonyl group having 2 to 10 carbon atoms, a dialkylaminocarbonyl group having 3 to 12 carbon atoms, an aralkyl group having 7 to 15 carbon atoms, an aralkyloxyl group having 7 to 15 carbon atoms, a dialkylamino group having 2 to 8 carbon atoms, or phenoxyl group; X is hydrogen, chlorine or bromine atom, and Y is chlorine or bromine atom; or with (b) a carboxylic acid represented by the formula (III)

RCOOH          (III)

wherein R has the same meaning as defined above, in the presence of an acid anhydride represented by the formula (IV)

(XYCHCO)$_2$O          (IV)

wherein X and Y have the same meanings as defined above.

The reaction is conducted usually in an solvent for which such halogenated hydrocarbons as carbon tetrachloride, tetrachloroethylene and tetrachloroethane are preferably used. The solvent may be employed alone or in a mixture of more than two solvents, and the amount of solvent is not critical.

As the catalyst, boron trifluoride or a boron trifluoride complex is used, and the boron trifluoride complex includes boron trifluoride-diethyl ether complex, boron trifluoride-methanol complex, boron trifluoride-acetic acid complex, and the like.

Aromatic compounds employed as raw materials of the present invention are those applicable to Friedel-Crafts Reaction, which are exemplified as follows;

(a) benzene, biphenyl, terphenyl, naphthalene and anthracene, in which benzene, biphenyl and terphenyl are substituted once to four times by a substituent containing at least one electron-donative group, and naphthalene and anthracene are unsubstituted or substituted once to four times by substitutents containing at least one electron-donative group, (b) a thiophene derivative having not more than three substituents, (c) pyrrol and a pyrrole derivative having a substituent at the nitrogen atom and/or having substituents of not more than two at the carbon atom, (d) a furan derivative represented by the formula wherein $R_1$, $R_2$ or $R_3$ denotes a substituent, (e) a heteroatom-containing aromatic compound represented by the formula wherein $R_1$, $R_2$ or $R_3$ denotes a substituent, $R_4$ denotes hydrogen atom, a lower alkyl or an acyl group, and n denotes an integer of 1 to 4, and (f) a condensed ring aromatic compound represented by the formula wherein $R_1$, $R_2$ or $R_3$ denotes a substituent, $R_4$ denotes a lower alkyl group or an acyl group with the proviso that at least one of substituent is a "electron-donative group", and n denotes an integer of 1 to 4.

In the above explanation on the aromatic compound, the term "electron-donative group" implies the following group;

(a) an alkyloxy group, alkenyloxy group and alkynyloxy group having respectively a straight chained or branched $C_1$-$C_{12}$ alkyl, alkenyl or alkynyl group, (b) a straight chained or branched $C_1$-$C_{12}$ alkanoyloxy group, (c) a straight chained or branched $C_8$-$C_{15}$ aralkanoyloxy group, (d) a substituted or unsubstituted $C_7$-$C_{18}$ aralkyloxy group, (e) an alkylthio group and alkylcarbonylthio group having $C_1$-$C_{12}$ alkyl, (f) an alkylcarbonylalkoxy group having 3 to 12 carbon atoms, (g) an alkylcarbonyloxyalkyl group having 3 to 12 carbon atoms, (h) an alkyloxyalkoxy group having 2 to 12 carbon atoms, (i) an alkyloxycarbonylalkoxy group having 3 to 12 carbon atoms, (j) an alkylcarbonyloxyalkoxy group having 3 to 12 carbon atoms, (k) a halogen atom, (l) methylenedioxy, ethylenedioxy and phenoxy, (m) a dialkylamino, an alkylamino, pyridino, pyrimidino, morpholino and N-(lower)alkylpyrrolidino.

Furthermore, the substituent includes the above "electron-donative group" and the following group;

(a) $C_1$-$C_{12}$ alkyl, $C_2$-$C_{12}$ alkenyl and $C_2$-$C_{12}$ alkynyl, (b) $C_7$-$C_{18}$ aralkyl with/without substituent, (c) an alkanoylalkyl and alkoxycarbonylalkyl group having 3 to 12 carbon atoms, (d) $C_1$-$C_{12}$ acylamino, (e) an alkoxyalkyl group having 2 to 12, and (f) an aralkylcarbonyloxyalkyl group having 9 to 15 carbon atoms.

In the process, though the amount of catalyst to be used is generally from 0.05 to 1 equivalents based on the mixed acid anhydride (II), the reaction proceeds even in an amount of catalyst of from 0.05 to 0.2. The amount of aromatic compound is 1.0 or more equivalents, preferably from 1.2 to 2 equivalents based on the mixed acid anhydride (II), however, an increased amount of the mixed acid anhydride may can be employed in case of the aromatic compound is more expensive. The reaction temperature is in a range of generally from −5° to 120° C., preferably from 20° to 90° C. The reaction time is generally in a range of from 0.5 to 20 hours, but it is not particularly limited.

The mixed acid anhydride represented by the formula (II), which is one of starting materials for the above-mentioned reaction, can be produced by reacting the above-mentioned carboxylic acid RCOOH (III) with a haloacetic acid compound represented by the formula (V)

XYCHCOZ (V)

wherein Z is hydroxyl group, chlorine or bromine atom, and X and Y are as defined above.

The carboxylic acid represented by the formula (III) may include their optical isomers, and they are exemplified by acetic acid, propionic acid, butyric acid, isobutyric acid, valeric acid, isovaleric acid, hexanoic acid, heptanoic acid, octanoic acid, lauric acid, decanoic acid, stearic acid, β-halopropionic acid (halo denotes fluorine, chlorine, bromine or iodine atom), β-halopropionic acid, γ-halovaleric acid, 2-methylpropionic acid, 2-methylhexanoic acid, 2-methylocatnoic acid, 2-halo-3-methylpentanoic acid, S(+)-2-methylbutanoic acid, acrylic acid, crotonic acid, trans-2-pentenoic acid, 4-pentenoic acid, tarns-2-hexenoic acid, trans-3-hexenoic acid, cis-3-hexenoic acid, trans-2-methyl-2-pentenoic acid, 4-pentynoic acid, 2-octenoic acid, 2-octyonoic acid, ω-halo-5-cisheptenoic acid, undecylenic acid, oleic acid, farnesyl acetic acid, cyclopropane carboxylic acid, (+)-2,2-dimethylcyclopropane carboxylic acid, cyclopentane carboxylic acid, cyclohexane carboxylic acid, methylcyclopentane carboxylic acid, 2-cyclohexene-1-carboxylic acid, cyclohexyl acetic acid, cyclohexyl butyric acid, benzoic acid, 4-methylbenzoic acid, 2,4-dimethylbenzoic acid, 4-methoxybenzoic acid, 4-octyloxybenzoic acid, 2,4-dichlorobenzoic acid, 4-bromobenzoic acid, 3,4-dimethoxybenzoic acid, 3,4-methylenedioxybenzoic acid, 3,4-dibenzyloxybenzoic acid, 2,4-dichlorobenzoic acid, 3,4,5-trimethoxybenzoic acid, 4-acetyloxybenzoic acid, 3,4-diacetyloxybenzoic acid, 4-acetylbenzoic acid, 4-propionylbenzoic acid, 4-methoxycarbonylbenzoic acid, 3-ethoxycarbonylbenzoic acid, thiophene carboxylic acid, phenyl acetic acid, 3-phenyl propionic acid, phenoxy acetic acid, 4-chlorophenyl acetic acid, α-chlorophenyl acetic acid, 4-chloro-α-isopropylphenyl acetic acid, 4-methylphenyl acetic acid, 4-methoxyphenyl acetic acid, α-phenyl propionic acid, 2-thienyl acetic acid, 4-(2-thienyl) butyric acid, 3-methoxy propionic acid, 5-ethoxy pentanoic acid, butoxy pentanoic acid, 6-methoxy hexanoic acid, monomethyl succinate, monomethyl glutarate, monomethyl suberate, levulinic acid, β-acetyloxy propionic acid, 10-oxo undecanoic acid, biphenylyl acetic acid, naphthalene carboxylic acid, furan carboxylic acid and 4'-octyloxy-4-carboxylbiphenyl.

When a haloacetic acid of the formula (V) in which substituent Z is hydroxyl group is used as the haloacetic acid compound, the aimed mixed acid anhydride can be obtained by the dehydration reaction in the presence or absence of a dehydrating agent, however, the aimed compound is easily available by the reaction using a haloacetyl halide in which the substituent Z is chlorine or bromine atom in the presence of an organic base and in a solvent. In the latter reaction, the amount of haloacetyl halide is generally from 1 to 1.5 equivalents based on the carboxylic acid. The organic base used in this reaction includes triethylamine, pyridine, diethylaniline and the like, and the amount thereof is generally from 1 to 1.5 equivalents based on the carboxylic acid. The reaction temperature is generally in a range of from −20° to 50° C. The reaction time is generally in a range of from 0.5 to 10 hours, but it is not particularly limited.

The reaction mixture obtained is subjected to filtration for separating off the resulting hydrochloride or hydrobromide salt of organic base to obtain crude solution of the mixed acid anhydride, which is then purified to obtain the mixed acid anhydride. The crude solution mentioned above can be used as it is for the next reaction with a aromatic compound. Accordingly, it is advantageous to use a solvent same as the solvent used in the next step.

In the case of the process (b) mentioned above, same carboxylic acids as exemplified for carboxylic acids of (III) may be used, and the acid anhydride (IV) includes, for example, chloroacetic anhydride, bromoacetic anhydride, dichloroacetic anhydride and the like. The amount of aromatic compound is 1.0 equivalent or more, preferably from 1.2 to 1.5 equivalents based on the carboxylic acid (III), however, an increased amount of the carboxylic acid may be employed in case of the aromatic compound is more expensive. The amount of acid anhydride (IV) is 1.0 equivalent or more, preferably from 1.1 to 1.3 equivalents based on the carboxylic acid (III). Although the amount of the boron trifluoride or boron trifluoride complex catalyst is generally from 0.02 to 0.2 equivalents based on the carboxylic acid (III), this amount is not restrictive and may be used in an amount of more than the above-mentioned amount. The reaction temperature is generally in a range of from −5° to 150° C., preferably from 20° to 90° C. The reaction time is generally in a range of from 0.5 to 20 hours, but it is not particularly limited.

The reaction mixture thus obtained is post-treated in usual manners and then purified by methods such as distillation, column chromatography or the like, if necessary, to obtain in high yield the aimed acylated derivatives of aromatic compounds.

Thus, according to the present invention, aimed acylaromatic compounds can be produced advantageously for the industry from a aromatic compound and a mixed acid anhydride (II) or a carboxylic acid (III). Moreover, since boron trifluoride, boron trifluoride complexes and acid anhydrides are commercially available cheeply, industrial value of the present invention is enhanced further.

The present invention will be illustrated in more detail below by way of showing Examples.

EXAMPLE 1

In 50 ml of dichloroethane were dissolved 9.41 g (0.05 mole) of suberic acid monomethyl ester and 9.83 g (0.0575 mole) of monochloroacetic anhydride. To the resulting solution were added 5.47 g (0.065 mole) of thiophene and 0.71 g of boron trifluoride-diethyl ether complex and the resulting mixture was then stirred at 60° C. for 5 hours. After completion of the reaction, the reaction solution was cooled and washed successively with water, 5% aqueous sodium carbonate solution and water. The organic layer was dried over anhydrous magnesium sulfate and then concentrated under reduced pressure to obtain 11.5 g of 2-(7-methoxycarbonyl-1-oxoheptyl)thiophene.

Yield: 91%.

EXAMPLE 2

Reaction and post-treatment were carried out in the same manner as in Example 1, except that 6.38 g (0.065 mole) of 2-methylthiophene and 6.4 g (0.05 mole) of cyclohexane carboxylic acid were substituent for the thiophene and the suberic acid monomethyl ester, to obtain 8.3 g of 2-cyclohexylcarbonyl-5-methylthiophene.

Yield: 80%.

EXAMPLE 3

Reaction and post-treatment were carried out in the same manner as in Example 1, except that 10.6 g (0.065 mole) of 2-bromothiophene and 6.1 g (0.05 mole) of benzoic acid were substituent for the thiophene and the suberic acid monomethyl ester, to obtain 6.95 g of 2-benzoyl-5-bromothiophene.

Yield: 52%.

EXAMPLE 4

In 40 ml of dichloroethane were dissolved 6.51 g (0.05 mole) of heptanoic acid and 10.26 g (0.06 mole) of monochloroacetic anhydride. To the resulting solution were added 7.57 g (0.07 mole) of anisole and 0.9 g of boron trifluoride-acetic acid complex and the resulting mixture was then stirred at refluxing for 8 hours. After completion of the reaction, the reaction solution was cooled and washed successively with water, 5% aqueous sodium carbonate solution and water. The organic layer was concentrated under reduced pressure to obtain 9.25 g of 4-methoxy-1-heptanoyl-benzene.

Yield: 84%.

EXAMPLE 5

In 50 ml of dichloroethane were dissolved 5.8 g (0.05 mole) of levulinic acid and 10.26 g (0.06 mole) of monochloroacetic anhydride. To the resulting solution were added 8.98 g (0.065 mole) of 1,2-dimethoxybenzene and 0.71 g of boron trifluoride-diethyl ether complex and the resulting mixture was then stirred at 50° C. for 5.5 hours. After completion of the reaction, the reaction solution was cooled and washed successively with water, 5% aqueous sodium carbonate solution and water. The organic layer was dried over anhydrous magnesium sulfate and then concentrated under reduced pressure to obtain 9.66 g of 4-(β-acetylpropionyl)-1,2-dimethoxybenzene.

Yield: 76%.

EXAMPLES 6 TO 10

Reaction and post-treatment were carried out in the same manner as in Example 1, except that each carboxylic acid (0.05 mole) shown in Table 1 was a substituent for suberic acid monomethyl ester in Example 1, to obtain results shown in Table 1.

TABLE 1

| | Starting carboxylic acid | | Acylated product | | |
|---|---|---|---|---|---|
| Example No. | Name of compound | Amount used (g) | Amount produced (g) | Yield (%) | Name of compound |
| 6 | 4-chlorophenyl acetic acid | 8.53 | 11.4 | 96 | 2-(4-chlorophenyl)-acetylthiophene |
| 7 | cyclohexyl butyric acid | 6.51 | 11 | 93 | 2-(cyclohexylbutyryl) thiophene |
| 8 | 4-pentic acid | 4.9 | 6.65 | 81 | 2-(4-pentynoyl) thiophene |
| 9 | trans-3-hexenic acid | 5.7 | 7.75 | 86 | 2-(trans-3-hexenoyl)-thiophene |
| 10 | 2-thienyl acetic acid | 7.11 | 9.37 | 90 | 2-(2-thienylacetyl) thiophene |

EXAMPLE 11

In 50 ml of dichloroethane were dissolved 3.7 g (0.05 mole) of propionic acid and 10.26 g (0.06 mole) of monochloroacetic anhydride. To the resulting solution were added 5.36 g (0.065 mole) of octyloxybenzene and 0.71 g of boron trifluoride-diethyl ether complex and the resulting mixture was then stirred at 70° C. for 5 hours. After completion of the reaction, the reaction solution was cooled and washed successively with water, 5% aqueous sodium carbonate solution and water. The organic layer was dried over anhydrous magnesium sulfate and then concentrated under reduced pressure to obtain 7.2 g of 4-octyloxypropiophenone.

Yield: 55%.

EXAMPLE 12

In 50 ml of dichloroethane were dissolved 6.51 g (0.05 mole) of heptanoic acid and 10.26 g (0.06 mole) of monochloroacetic anhydride. To the resulting solution were added 4.36 g (0.065 mole) of pyrrole and 0.71 g of boron trifluoride-diethyl ether complex and the resulting mixture was then stirred at 50° C. for 5.5 hours. After completion of .the reaction, the reaction solution was cooled and washed successively with water, 5% aqueous sodium carbonate solution and water. The organic layer was dried over anhydrous magnesium sulfate and then concentrated under reduced pressure to obtain 5.74 g of 2-heptanoyl-pyrrole.

Yield: 64%.

EXAMPLE 13

In 50 ml of tetrachloroethane were dissolved 5.1 g (0.05 mole) of 2S-methyl butyric acid and 14.39 g (0.06 mole) of dichloroacetic anhydride. To the resulting solution were added 10.92 g (0.065 mole) of 1,2,3-trimethoxybenzene and 0.71 g of boron trifluoridediethyl ether complex and the resulting mixture was then stirred at 50° C. for 3 hours. After completion of the reaction, the reaction solution was cooled and washed successively with water, 5% aqueous sodium carbonate solution and water. The organic layer was dried over anhydrous magnesium sulfate and then concentrated under reduced pressure to obtain 10.1 g of 3,4,5-trimethoxyphenyl (1-methylpropyl)ketone.

Yield: 80%.

EXAMPLE 14

In 50 ml of dichloroethane were dissolved 8.51 g (0.05 mole) of 4-(2-thienyl)butyric acid and 14.39 g (0.06 mole) of dichloroacetic anhydride. To the resulting solution was added 0.065 mole of 3,5-dimethylfuran and 0.71 g of boron trifluoride-diethyl ether complex and the resulting mixture was then stirred at 50° C. for 7 hours. After completion of the reaction, the reaction solution was cooled and washed successively with 5% aqueous sodium carbonate solution and water. The organic layer was concentrated under reduced pressure to obtain 2-[4-(2-thienyl)butyryl]3,5-dimethylfuran.

Yield: 90%.

EXAMPLE 15

In 50 ml of dichloroethane were dissolved 7.51 g (0.05 mole) of β-phenylpropionic acid and 9.83 g (0.0575 mole) of monochloroacetic anhydride. To the resulting solution were added 8.17 g (0.06 mole) of phenylacetate and 1.0 g of boron trifluoride-acetic acid complex and the resulting mixture was then stirred at 90° C. for 8 hours. After completion of the reaction, the reaction solution was cooled and washed successively with water, 5% aqueous sodium carbonate solution and water. The organic layer was dried over anhydrous magnesium sulfate and then concentrated under reduced pressure to obtain 10.7 g of 4-acetyloxy-1-(β-phenyl)propionylbenzene.

Yield: 80%.

EXAMPLE 16

In 50 ml of dichloroethane were dissolved 7.31 g (0.05 mole) of 6-methoxy hexanoic acid and 14.39 g (0.06 mole) of dichloroacetic anhydride. To the resulting solution were added 7.93 g (0.065 mole) of methylenedioxybenzene and 0.71 g of boron trifluoridediethyl ether complex and the resulting mixture was then stirred at 70° C. for 6 hours. After completion of the reaction, the reaction solution was cooled and washed with 5% aqueous sodium carbonate solution and water in this order. The organic layer was concentrated under reduced pressure to obtain 11.2 g of 4-(6-methoxyhexanoyl)-1,2-methylenedioxybenzene.

EXAMPLE 17

In 50 ml of toluene were dissolved 4.31 g (0.05 mole) of crotonic acid, 5.47 g (0.065 mole) of thiophene and 10.26 g (0.06 mole) of monochloroacetic anhydride. To the resulting solution was added 0.71 g of boron trifluoride-diethyl ether complex and the resulting mixture was stirred at 50° C. for 6.5 hours. After completion of the reaction, the reaction solution was cooled and washed with 5% aqueous sodium carbonate solution and water in this order. The organic layer was concentrated under reduced pressure to obtain 4.26 g of 2-crotonylthiophene.

Yield: 56%.

EXAMPLE 18

Reaction and post-treatment were carried out in the same manner as in Example 12, except that 5.27 g (0.065 mole) of 1-methylpyrrole and 4.4 g (0.05 mole) of isobutyric acid were substituent for the pyrrole and heptanoic acid, to obtain 6 g of 1-methyl-2-isobutyrylpyrrole.

Yield: 80%.

EXAMPLES 19 TO 22

Reaction and post-treatment were carried out in the same manner as in Example 1, except that each carboxylic acid shown in Table 2 was a substituent for suberic acid monomethyl ester in Example 1, to obtain results shown in Table 2.

TABLE 2

| Example No. | Starting carboxylic acid | | Acylated product | | |
|---|---|---|---|---|---|
| | Name of compound | Amount used (g) | Amount produced (g) | Yield (%) | Name of compound |
| 19 | 4-methyl benzoic acid | 6.81 | 5.26 | 52 | 4-methylbenzoyl thiophene |
| 20 | 4-bromo benzoic acid | 10.01 | 5.88 | 44 | 4-bromobenzoyl thiophene |
| 21 | thiophene carboxylic acid | 6.41 | 5.73 | 59 | 2,2-dithienyl ketone |

TABLE 2-continued

| Example No. | Starting carboxylic acid | | Acylated product | | |
|---|---|---|---|---|---|
| | Name of compound | Amount used (g) | Amount produced (g) | Yield (%) | Name of compound |
| 22 | cyclopropane carboxylic acid | 4.3 | 6.09 | 80 | cyclopropyl-2-thienyl ketone |

EXAMPLE 23

Reaction and post-treatment were carried out in the same manner as in Example 14, except that 10-acetyloxydecanoic acid was a substituent for 4-(2-thienyl)-butyric acid, to obtain 2-(10-acetyloxydecanoyl)-3,5-dimethylfuran.

Yield: 90%.

EXAMPLE 24

Reaction and post-treatment were carried out in the same manner as in Example 15, except that 5.71 g (0.05 mole) of (+)-2,2-dimethylcyclopropanecarboxylic acid was a substituent for β-phenylpropionic acid, to obtain 8.83 g of acetyloxyphenyl-2,2-dimethylcyclopropylketone.

Yield: 76%.

EXAMPLES 25 TO 26

Reaction and post-treatment were carried out in the same manner as in Example 1, except that each carboxylic acid shown in Table 3 was a substituent for suberic acid monomethyl ester in Example 1, to obtain results shown in Table 3.

TABLE 3

| Example No. | Starting carboxylic acid | | Acylated product | | |
|---|---|---|---|---|---|
| | Name of compound | Amount used (g) | Amount produced (g) | Yield (%) | Name of compound |
| 25 | β-chloropropionic acid | 5.43 | 4.63 | 53 | 2-(β-chloropropionyl)-thiophene |
| 26 | stearic acid | 14.21 | 16.3 | 93 | 2-(octadecanoyl)-thiophene |

EXAMPLE 27

In 50 ml of tetrachloroethane were dissolved 6.51 g (0.05 mole) of heptanoic acid and 9.83 g (0.0575 mole) of monochloroacetic anhydride. To the resulting solution were added 12.74 g (0.06 mole) of 4-acetoxybiphenyl and 0.8 g of boron trifluoride-diethyl ether complex and the resulting mixture was then stirred at 100° C. for 10 hours. After completion of the reaction, the reaction solution was cooled and washed with 5% aqueous sodium carbonate solution and water in this order. The organic layer was concentrated under reduced pressure to obtain 12.0 g of 4-acetoxy-4'-heptanoylbiphenyl.

Yield: 74%.

EXAMPLE 28

In 50 ml of dichloroethane were dissolved 11.51 g (0.05 mole) of 10-acetyloxydecanoic acid and 14.39 g (0.06 mole) of dichloroacetic anhydride. To the resulting solution were added 9.89 g (0.065 mole) of 3,4-dimethoxytoluene and 0.71 g of boron trifluoridediethyl ether complex and the resulting mixture was then stirred at 75° C. for 5 hours. After completion of the reaction, the reaction solution was cooled and washed successively with water, 5% aqueous sodium carbonate solution and water. The organic layer was dried over anhydrous magnesium sulfate and then concentrated under reduced pressure to obtain 15.3 g of 3,4-dimethoxy-6-(10-acetyloxydecanoyl)toluene.

Yield: 84%.

EXAMPLE 29

In 50 ml of tetrachloroethane were dissolved 4.41 g (0.05 mole) of butyric acid and 9.83 g (0.0575 mole) of monochloroacetic anhydride. To the resulting solution were added 7.69 g (0.06 mole) of naphthalene and 0.9 g of boron trifluoride-diethyl ether complex and the resulting mixture was then stirred at 115° C. for 8 hours. After completion of the reaction, the reaction solution was cooled and washed successively with water, 5% aqueous sodium carbonate solution and water. The organic layer was dried over anhydrous magnesium sulfate and then concentrated under reduced pressure to obtain 4.26 g of butyrylnaphthalene.

Yield: 43%.

EXAMPLE 30

In 50 ml of dichloroethane were dissolved 10.6 g (0.05 mole) of 3,4,5-trimethoxybenzoic acid and 9.83 g (0.0575 mole) of monochloroacetic anhydride. To the resulting solution were added 5.47 g (0.065 mole) of thiophene and 0.71 g of boron trifluoride-diethyl ether complex and the resulting mixture was then stirred at 65° C. for 6 hours. After completion of the reaction, the reaction solution was cooled and washed successively with water, 5% aqueous sodium carbonate solution and water. The organic layer was dried over anhydrous magnesium sulfate and then concentrated under reduced pressure to obtain 5.77 g of 2-(3,4,5-trimethoxybenzoyl)thiophene.

Yield: 41.5%.

EXAMPLE 31

In 50 ml of dichloroethane were dissolved 10.5 g (0.05 mole) of 11-cyanoundecanoic acid and 10.26 g (0.06 mole) of monochloroacetic anhydride. To the resulting solution were added 8.98 g (0.065 mole) of 1,2-dimethoxybenzene and 0.71 g of boron trifluoridediethyl ether complex and the resulting mixture was then stirred at 75° C. for 6 hours. After completion of the reaction, the reaction solution was cooled and washed successively with water, 5% aqueous sodium carbonate solution and water. The organic layer was dried over anhydrous magnesium sulfate and then concentrated under reduced pressure to obtain 14.2 g of 4-(11-cyanoundecanoyl)-1,2-dimethoxybenzene.
Yield: 86%.

EXAMPLE 32

In 50 ml of dichloroethane were dissolved 6.31 g (0.05 mole) of 1-cyclohexene-1-carboxylic acid and 10.26 g (0.06 mole) of monochloroacetic anhydride. To the resulting solution were added 8.98 g (0.065 mole) of 1,2-dimethoxybenzene and 0.71 g of boron trifluoridediethyl ether complex and the resulting mixture was then stirred at 75° C. for 6 hours. After completion of the reaction, the reaction solution was cooled and washed successively with water, 5% aqueous sodium carbonate solution and water. The organic layer was dried over anhydrous magnesium sulfate and then concentrated under reduced pressure to obtain 7.27 g of 4-(1-cyclohexenoyl)-1,2-dimethoxybenzene.
Yield: 59%.

EXAMPLE 33

In 50 ml of tetrachloroethane were dissolved 12.5 g (0.05 mole) of 4-octyloxybenzoic acid and 14.39 g (0.06 mole) of dichloroacetic anhydride. To the resulting solution were added 11.1 g (0.06 mole) of benzylphenyl ether and 0.71 g of boron trifluoride-diethyl ether complex and the resulting mixture was then stirred at 105° C. for 7 hours. After completion of the reaction, the reaction solution was cooled and washed successively with water, 5% aqueous sodium carbonate solution and water. The organic layer was dried over anhydrous magnesium sulfate and then concentrated under reduced pressure to obtain 13.74 g of 4-(4-octyloxybenzoyl)phenylbenzyl ether.
Yield: 66%.

EXAMPLE 34

In 50 ml of tetrachloroethane were dissolved 5.11 g (0.05 mole) of valeric acid and 9.83 g (0.0575 mole) of monochloroacetic anhydride. To the resulting solution were added 9.42 g (0.06 mole) of bromobenzene and 0.8 g of boron trifluoride-diethyl ether complex and the resulting mixture was then stirred at 115° C. for 10 hours. After completion of the reaction, the reaction solution was cooled and washed successively with water, 5% aqueous sodium carbonate solution and water. The organic layer was dried over anhydrous magnesium sulfate and then concentrated under reduced pressure to obtain 6.75 g of valerylbromobenzene.
Yield: 56%.

EXAMPLE 35

Reaction and post-treatment were carried out in the same manner as in Example 1, except that 9.71 g (0.05 mole) of 4-acetoxyphenylacetic acid was a substituent for suberic acid monomethyl ester, to obtain 10.0 g of 2-(4-acetoxyphenylacetyl)thiophene.
Yield: 77%.

EXAMPLE 36

A four neck flask equipped with a stirrer and a thermometer was charged with 9.41 g (0.05 mole) of suberic acid monomethyl ester, 5.11 g (0.0505 mole) of triethylamine and 60 ml of carbon tetrachloride. Under stirring, 5.71 g (0.0505 mole) of monochloroacetyl chloride was added dropwise thereto at 0° to 5° C. After completion of dropping, the reaction was continued at room temperature for 3 hours. After completion of the reaction, the reaction mixture was filtered under reduced pressure to remove formed hydrochloride salt of triethylamine.

To the filtrate were added 0.075 mole of thiophen and 0.71 g (0.005 mole) of boron trifluoridediethyl ether complex and the resulting mixture was heated at 40° C. for 4 hours. After completion of the reaction, the reaction solution was cooled and washed successively with 50 ml of water, 50 ml of 5% aqueous sodium carbonate solution and 50 ml of water. The organic layer was dried over anhydrous magnesium sulfate and then concentrated under reduced pressure to obtain 2-(7-methoxycarbonyl-1-oxoheptyl)thiophene.
Yield: 82%.

EXAMPLE 37

A four neck flask equipped with a stirrer and a thermometer was charged with 3.7 g (0.05 mole) of propionic acid, 5.11 g (0.050 mole) of triethylamine and 60 ml of carbon tetrachloride. Thereto was added dropwise 0.0505 mole of dichloroacetyl chloride at 0° to 5° C. After completion of dropping, the reaction mixture was filtered under reduced pressure to remove formed hydrochloride salt of triethylamine.

To the filtrate were added 0.065 mole of 3,5-dimethylfuran and 1.0 g of boron trifluoride-acetic acid complex and the resulting mixture was stirred at 50° C. for 6 hours. After completion of the reaction, post-treatment was carried out in the same manner as in Example 1 to obtain 2-propionyl-3,5-dimethylfuran.
Yield: 41.5%.

EXAMPLES 38–45

Reactions and post-treatments were carried out in the same manner as in Example 28, except that each carboxylic acid shown in Table 4 was a substituent for 10-acetyloxydecanoic acid to obtain results shown in Table 4.

TABLE 4

| Example No. | Starting carboxylic acid | Acylated product |
|---|---|---|
| 38 | 4-(1-cyclohexenyl-oxy)benzoic acid | 3,4-dimethoxy-6-[4-(1-cyclohexenyloxy)benzoyl]-toluene |
| 39 | 4-phenylbutanoic acid | 3,4-dimethoxy-6-(4-phenylbutanoyl)toluene |
| 40 | 4-biphenyl-carboxylic acid | 3,4-dimethoxy-6-(4-biphenylcarbonyl)-toluene |
| 41 | 3-furyl-propionic acid | 3,4-dimethoxy-6-(3-furylpropanoyl)-toluene |
| 42 | 4-methylthio-benzoic acid | 3,4-dimethoxy-6-(4-methylthiobenzoyl)-toluene |
| 43 | 3-(benzoyl)-propionic acid | 3,4-dimethoxy-6-[3-(benzoyl)propanoyl]-toluene |
| 44 | 3,4-methylene-dioxybenzoic acid | 3,4-dimethoxy-6-(3,4-methylenedioxybenzoyl)-toluene |
| 45 | 3-methylthio-propionic acid | 3,4-dimethoxy-6-(3-methylthiopropanoyl)-toluene |

EXAMPLES 46–50

Reactions and post-treatments were carried out in the same manner as in Example 31, except that each carboxylic acid shown in Table 5 was a substituent for 11-cyanoundecanic acid, to obtain results shown in Table 5.

TABLE 5

| No. | Starting carboxylic acid | Acylated product |
|---|---|---|
| 46 | 3-acetylthio-propionic acid | 4-(3-acetylthiopropanoyl)-1,2-dimethoxybenzene |
| 47 | cyclohexyl-propenoic acid | 4-(cyclohexylpropenoyl)-1,2-dimethoxybenzene |
| 48 | 1-naphthylacetic acid | 4-(1-naphthylaceto)-1,2-dimethoxybenzene |
| 49 | 4-benzyloxybenzoic acid | 4-(4-benzyloxybenzoyl)-1,2-dimethoxybenzene |
| 50 | 2-furoic acid | 4-(2-furoyl)-1,2-dimethoxybenzene |

EXAMPLES 51-52

Reactions and post-treatments were carried out in the same manner as in Example 12, except that each aromatic compound shown in Table 6 was a substituent for pyrrole to obtain results shown in Table 6.

TABLE 6

| Example No. | Starting aromatic compound | Acylated product |
|---|---|---|
| 51 | benzothiophene | 2-heptanoylbenzothiophene |
| 52 | benzofuran | 2-heptanoylbenzofuran |

What is claimed is:

1. A process for producing an acylaromatic compound represented by the formula (I)

     (I)

which comprises reacting an aromatic compound, in the presence of boron trifluoride or a boron trifluoride complex catalyst, with either a) a mixed acid anhydride represented by the formula (II)

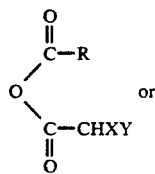     (II)

b) a carboxylic acid represented by the formula (III)

RCOOH     (III)

in the presence of an acid anhydride represented by the formula (IV)

(XYCHCO)$_2$O     (IV), in a liquid phase, wherein
Q is an aromatic compound residue;
R is a straight, branched or cyclic aliphatic group, aromatic group or araliphatic group;
X is hydrogen, chlorine or bromine; and
Y is chlorine or bromine.

2. A process for producing an acylaromatic compound represented by the formula (I)

     (I)

which consists of reacting an aromatic compound, in the presence of boron trifluoride or a boron trifluoride complex catalyst, with either a) a mixed acid anhydride represented by the formula (II)

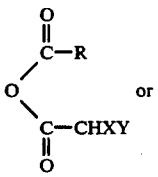     (II)

b) a carboxylic acid represented by the formula (III)

RCOOH     (III)

in the presence of an acid anhydride represented by the formula (IV)

(XYCHCO)$_2$O     (IV), in a liquid phase, wherein
Q is an aromatic compound residue;
R is a straight, branched or cyclic aliphatic group, aromatic group or araliphatic group;
X is hydrogen, chlorine or bromine; and
Y is chlorine or bromine.

3. A process for producing an acylaromatic compound represented by the formula (I)

     (I)

which comprises reacting an aromatic compound, in the presence of boron trifluoride or a boron trifluoride complex, with either a) a mixed acid anhydride represented by the formula (II)

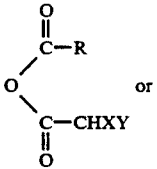     (II)

b) a carboxylic acid represented by the formula (III)

RCOOH     (III)

in the presence of an acid anhydride represented by the formula (IV)

(XYCHCO)$_2$O     (IV), in a liquid phase, wherein
Q is an aromatic compound residue;
R is a straight, branched or cyclic aliphatic group, aromatic group or araliphatic group;
X is hydrogen, chlorine or bromine; and Y is chlorine or bromine;
and wherein the acid anhydride is present in an amount of 1.1 to 1.3 mole times the amount of the carboxylic acid (III) the amount of the boron trifluoride or boron trifluoride complex catalyst is 0.05 to 1.0 mole times the amount of the mixed acid anhydride (II);
or 0.02 to 0.2 mole times the amount of the carboxylic acid (III).

4. A process according to claim 1, wherein said mixed acid anhydride represented by the formula

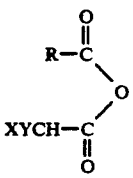

is produced by reacting a carboxylic acid represented by the formula

RCOOH with a haloacetic acid compound represented by the formula

XYCHOZ wherein R, X and Y have the same meaning as in claim 1, and Z is a hydroxyl, chlorine or bromine.

5. A process according to claim 1, wherein the boron trifluoride complex is boron trifluoride-diethyl ether complex, boron trifluoride-acetic acid complex or boron trifluoride-methanol complex.

6. A process according to claim 1, wherein the amount of said catalyst is from 0.05 to 1 equivalents based on said mixed acid anhydride.

7. A process according to claim 1, wherein the amount of said catalyst is from 0.02 to 0.2 equivalents based on said carboxylic acid.

8. A process according to claim 1, wherein the amount of said aromatic compound is from 1.2 to 2 equivalents based on said mixed acid anhydride.

9. A process according to claim 1, wherein the amount of said aromatic compound is from 1.2 to 2 equivalents based on said carboxylic acid.

10. A process according to claim 1, wherein the amount of said acid anhydride is from 1.1 to 1.3 equivalents based on said carboxylic acid.

11. A process according to claim 1 or 4, wherein said carboxylic acid is benzoic acid.

12. A process according to claim 4, wherein the substituent Z of said haloacetic acid compound is chlorine or bromine atom.

13. A process according to claim 12, wherein said reaction is carried out in the presence of an organic base.

14. A process according to claim 13, wherein said organic base is triethylamine, pyridine or diethylaniline.

15. A process according to claim 12, wherein the amount of said haloacetic acid compound is from 1 to 1.5 equivalents based on said carboxylic acid.

16. A process according to claim 13, wherein the amount of said organic base is from 1 to 1.5 equivalents based on said carboxylic acid.

17. A process according to claim 12, wherein the reaction temperature is in a range of from −20° to 50° C.

18. A process according to claim 1, wherein the reaction temperature is either in a range of from −5° to 120° C. when the reaction is carried out with said mixed acid anhydride, or in a range from −5° to 150° C. when the reaction is carried out with said carboxylic acid and acid anhydride.

19. A process according to claim 1 or 4, wherein said carboxylic acid is selected from the group consisting of alkylcarboxylic acid having 2 to 19 carbon atoms, cyclic alkyl, carboxylic acid having 4 to 9 carbon atoms, and cycloalkylalkyl carboxylic acid having 5 to 16 carbon atoms.

20. A process according to claim 1 or 4, wherein said carboxylic acid is selected from the group consisting of alkenyl carboxylic acid or alkynyl carboxylic acid having 3 to 19 carbon atoms, cyclic alkenyl carboxylic acid or cyclic alkynyl carboxylic acid having 4 to 9 carbon atoms, cycloalkenylalkyl carboxylic acid or cycloalkynylalkyl carboxylic acid having 5 to 16 carbon atoms, and cycloalkylalkenyl carboxylic acid, cycloalkylalkyl carboxylic acid, cycloalkenylalkeny carboxylic acid or cycloalkenylalkynyl carboxylic acid having 6 to 16 carbon atoms.

21. A process according to claim 1 or 4, wherein said carboxylic acid is cyclic alkyl carboxylic acid having 4 to 9 carbon atoms.

22. A process according to claim 1 or 4, wherein R is selected from the group consisting of thienylalkyl or furylalkyl having 5 to 19 carbon atoms, thienylalkenyl, carbon atoms, phenylalkyl having 7 to 21 carbon atoms, phenylalkenyl or phenylalkynyl having 8 to 21 carbon atoms, naphthylalkyl having 11 to 25 carbon atoms, naphthylalkenyl or naphthylalkynyl having 12 to 25 carbon atoms, biphenyllylalkyl having 13 to 27 carbon atoms, and biphenyllylalkenyl or biphenyllyalkynyl having 14 to 27 carbon atoms, which is unsubstituted or substituted on the aromatic ring once, twice, thrice or four times by alkyl or alkoxyl having 1 to 12 carbon atoms, alkenyl, alkynyl, alkenyloxyl or alkynyloxyl having 2 to 12 carbon atoms, methylenedioxy, ethylenedioxy, phenylalkyl or phenylalkyloxyl having 7 to 12 carbon atoms, phenoxyl, alkyloxycarbonyl or alkylcarbonyloxyl having 2 to 9 carbon atoms, or halogen.

23. A process according to claim 1 or 4, wherein said carboxylic acid is selected from the group consisting of alkyl carboxylic acid having 2 to 19 carbon atoms, and alkenyl carboxylic acid or alkynyl carboxylic acid having 3 to 19 carbon atoms, which is unsubstituted or substituted by alkoxy having 1 to 9 carbon atoms, or alkoxycarbonyl having 2 to 19 carbon atoms.

24. A process according to claim 1 or 4, wherein said carboxylic acid is benzoic acid substituted by one, two or three alkyl groups having 1 to 12 carbon atoms, alkoxy groups having 1 to 12 carbon atoms or halogen.

25. A process according to claim 1, wherein the boron trifluoride or boron trifluoride complex catalyst is present in an amount 0.05 to 1.0 mole times the amount of the mixed acid anhydride (II) or in an amount 0.02 to 0.2 mole times the amount of the carboxylic acid (III).

26. A process according to claim 1, wherein the acid anhydride (IV) is present in an amount 1.1 to 1.3 mole times the amount of the carboxylic acid (III).

* * * * *